US00PP22238P2

(12) United States Plant Patent
Ui et al.

(10) Patent No.: US PP22,238 P2
(45) Date of Patent: Nov. 8, 2011

(54) ***OSTEOSPERMUM* PLANT NAMED 'SAKOST021'**

(50) Latin Name: *Osteospermum hybrida*
Varietal Denomination: SAKOST021

(75) Inventors: Akinobu Ui, Iwata (JP); Moriya Kawashima, Amstelveen (NL); Niels G. Kristensen, Silkeborg (DK)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/807,654

(22) Filed: Sep. 10, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Kent L Bell
(74) *Attorney, Agent, or Firm* — Jondle & Associates, P.C.

(57) ABSTRACT

A new *Osteospermum* plant particularly distinguished by having a yellow flower color, vigorous growth habit, plant structure with minimal branching, and an earliness to ray floret, is disclosed.

1 Drawing Sheet

Genus and species: *Osteospermum hybrida.*
Variety denomination: 'SAKOST021'.

BACKGROUND OF THE NEW PLANT

The present invention comprises a new and distinct cultivar of *Osteospermum,* botanically known as *Osteospermum hybrida,* and hereinafter referred to by the cultivar name 'SAKOST021'. 'SAKOST021' originated as a naturally occurring, whole plant mutation of 'Kakegawa AU20' (U.S. Plant Pat. No. 18,980) discovered in 2005 in Kakegawa, Japan. 'SAKOST021' has a deeper yellow flower color than that of 'Kakegawa AU20'.

From 2006 to 2007, the 'SAKOST021' was vegetatively propagated from cuttings and re-evaluated in an open field and in a greenhouse. The stability of the distinct characteristics of the new variety was confirmed. The selection was subsequently named 'SAKOST021'.

SUMMARY OF THE INVENTION

The following are the most outstanding and distinguishing characteristics of this new cultivar when grown under normal horticultural practices in Salinas, Calif.

1. yellow color;
2. vigorous growth habit;
3. plant structure with minimal branching; and
4. earliness to flower.

DESCRIPTION OF PHOTOGRAPHS

This new *Osteospermum* plant is illustrated by the accompanying photographs which show the plant's overall plant habit including form, foliage, and flowers. The photographs are of a plant grown three months from transplant date into 6-inch pots from rooted cuttings in Salinas, Calif. in the spring of 2010. The colors shown are as true as can be reasonably obtained by conventional photographic procedures.

DESCRIPTION OF THE NEW CULTIVAR

Figure 1:
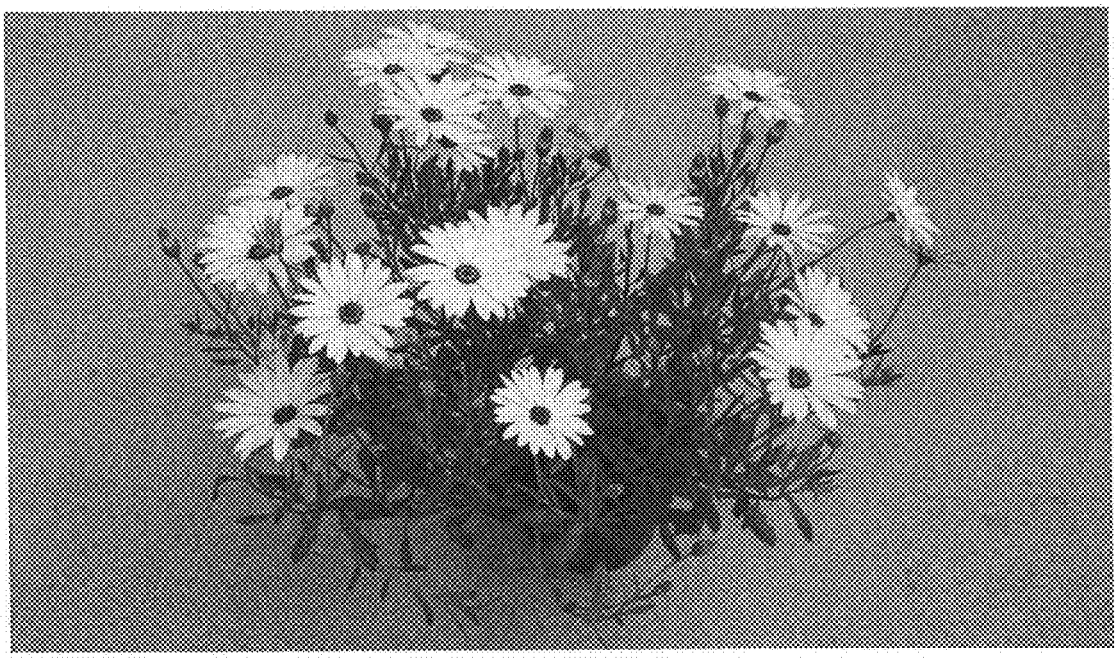
FIG. 1 shows overall plant habit of the plant grown in a pot.
Figure 2:
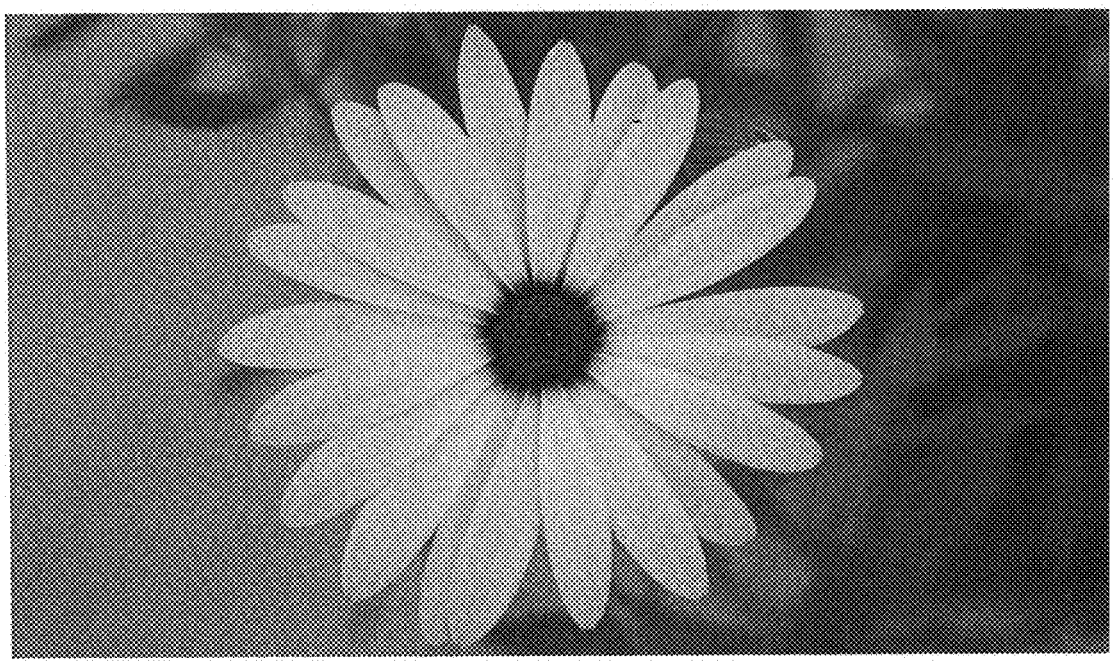
FIG. 2 shows the mature inflorescence of the plant.

The following detailed descriptions set forth the distinctive characteristics of 'SAKOST021'. The data which define these characteristics were collected from asexual reproductions carried out in Salinas, Calif. Data was collected on plants grown approximately three months from transplant date into 6-inch pots under greenhouse conditions in Salinas, Calif. in the spring of 2010. Color references are to The R.H.S. Colour Chart of The Royal Horticultural Society of London (R.H.S.), 4$^{th}$ edition.

DESCRIPTION OF THE NEW PLANT

Classification:

*Family.*—Compositae.

*Botanical.—Osteospermum hybrida.*

*Common.—Osteospermum,* Cape Daisy, South African Daisy.

*Designation.*—'SAKOST021'.

Parentage:

*Parent.—Osteospermum* plant 'Kakegawa AU20' (U.S. Plant Pat. No. 18,980)

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif., where the data was collected, range from 16° C. to 25° C.

*Time to bloom from propagation.*—Approximately four weeks when rooted vegetative cuttings are transferred to a 16 cm diameter pot. Flowering season is all year in the United States. Vernalization is not required to induce flowering.

Plant description:

*Habit.*—Vigorous.
*Life cycle.*—Perennial.
*Form.*—Erect.
*Height (from soil line to top of foliage).*—31.0 cm to 32.0 cm.
*Width.*—48.0 cm to 50.0 cm.

Stems:

*General.*—Circular in cross section; dull.
*Stem length (total).*—23.0 cm to 24.0 cm.
*Diameter.*—0.3 cm.
*Internode length.*—1.0 cm.
*Color.*—RHS 144A (Yellow-green).
*Pubescence.*—Slight. Color: RHS N155A (White). Shape: Linear.
*Anthocyanin color.*—None.

Branches:

*General.*—Circular cross section; dull.
*Number of main branches.*—One.
*Total number of branches.*—Four.
*Length.*—2.0 cm from soil line to first node.
*Diameter.*—0.6 cm.
*Internode length.*—2.0 cm.
*Color.*—RHS 144A (Yellow-green) with slight RHS N187A (Greyed-purple) anthocyanin.
*Pubescence.*—Absent.

Leaves:

*Arrangement.*—Alternate.
*Shape.*—Oblanceolate.
*Apex.*—Acute.
*Base.*—Attenuate.
*Margin.*—Serrate.
*Venation.*—Pinnate.
*Surface (both surfaces).*—Dull; smooth.
*Surface pubescence (both surfaces).*—Absent.
*Attachment.*—Decurrant.
*Length.*—8.0 cm.
*Width.*—2.5 cm.
*Thickness.*—Less than 0.1 cm.
*Color.*—Upper surface: RHS 137A (Green). Lower surface: RHS 138B (Green).
*Venation color.*—Upper surface: RHS 144A (Yellow-green). Lower surface: RHS 144B (Yellow-green).

Inflorescence:

*Number per plant.*—24 with multiple buds.
*Type.*—Capitulum (head); disc florets are perfect and ray florets are carpellate.
*Flowering habit.*—Determinate.
*Lastingness of inflorescences.*—3 to 4 days.
*Fragrance.*—Absent.
*Seed production.*—None observed.
*Diameter.*—9.0 cm.
*Depth.*—1.0 cm.
*Petal (ray floret) number.*—22 to 25 per inflorescence.
*Disc diameter.*—1.5 cm.
*Disc floret number.*—60 to 80 per inflorescence.
*Peduncle length.*—9.0 cm.
*Peduncle diameter.*—0.2 cm.
*Peduncle color.*—RHS 144A (Yellow-green).
*Peduncle texture.*—Dull; slight pubescence.
*Phyllaries.*—Arrangement: 22 per inflorescence; free; arranged symmetrically. Length: 1.5 cm to 1.7 cm. Width: 0.2 cm. Apex: Acute. Margin: Entire. Shape: Linear; acute. Color: Upper surface: RHS 137A (Green). Lower surface: RHS 137A (Green).

Ray florets (ligules):

*Corolla.*—Only the outer row of florets are the ray florets.
*Number of ray florets.*—22 to 25 per inflorescence.
*Length.*—4.0 cm.
*Width.*—1.0 cm.
*Shape.*—Lanceolate.
*Apex.*—Obtuse with a notched tip.
*Margin.*—Entire.
*Base.*—Fused.
*Color.*—Upper surface: RHS 9B (Yellow) with RHS N82A (Purple-violet) at base Lower surface: RHS 9B (Yellow) with wide RHS 163A (Greyed-orange) stripe in center.
*Pubescence.*—Glabrous.

Disc florets:

*Color.*—RHS 155A (White) with RHS 163A (Greyed-orange) and RHS N187B (Greyed-purple).
*Shape.*—Tubular.
*Apex.*—Rounded.
*Surface.*—Smooth; shiny.
*Size.*—Length: 0.7 cm. Width: 0.1 cm.

Reproductive organs:

*Ovary.*—Superior.
*Pistil form.*—One style with two stigma branches.
*Pistil length.*—0.4 cm.
*Stigma color.*—RHS N92A (Violet-blue).
*Style color.*—RHS 75A (Purple).
*Stamens.*—5; fused into a single tube.
*Anther color.*—RHS N187B (Greyed-purple).
*Pollen color.*—RHS 23A (Yellow-orange).
*Filament color.*—RHS 155A (White).

Disease and insect resistance: Very disease resistant. However, plants are susceptible to aphids, thrips, whiteflies, and worms.

COMPARISON WITH PARENTAL LINE AND KNOWN CULTIVAR

'SAKOST021' is a distinct variety of *Osteospermum* owing to its yellow color, vigorous growth habit, plant structure with minimal branching, and earliness to flower. 'SAKOST021' is distinguished from its parent 'Kakegawa AU20' (U.S. Plant Pat. No. 18,980) as described in Table 1 (color references are to The Royal Horticultural Society Colour Chart, 4$^{th}$ edition):

TABLE 1

| Comparison with 'Kakegawa AU20' | | |
|---|---|---|
| Characteristic | 'SAKOST021' | 'Kakegawa AU20' |
| Ray floret (ligule) color, upper surface | RHS 9B (Yellow) with RHS N82A (Purple-violet) at base | RHS 6D (Yellow) with RHS 155A (White) base that fades into RHS N79B (Purple) alongside the ray flowers and the very base of the petal |

'SAKOST021' is a distinct variety of *Osteospermum* owing to its yellow color, vigorous growth habit, plant structure with minimal branching, and earliness to flower. 'SAKOST021' is most similar to the *Osteospermum* plants named 'Seikilrem' (U.S. Plant Pat. No. 13,407). Differences between these varieties are described in Table 2 (color references are to The Royal Horticultural Society Colour Chart, 4th edition):

TABLE 2

| Comparison with 'Seikilrem' | | |
|---|---|---|
| Characteristic | 'SAKOST021' | 'Seikilrem' |
| Ray floret (ligule) color, upper surface | RHS 9B (Yellow) with RHS N82A (Purple-violet) at base | Yellow at apex RHS 12A; mid-section RHS 12B; towards base, a white band RHS 155C; below white band, a band of purple RHS 90D to RHS 90B; main color does not fade with subsequent development |

TABLE 2-continued

| Comparison with 'Seikilrem' | | |
|---|---|---|
| Characteristic | 'SAKOST021' | 'Seikilrem' |
| Plant growth habit | Less branching habit; vigorous growth performance | Compact and mounded plant habit; initially upright and then outwardly spreading; moderately vigorous |

We claim:

1. A new and distinct cultivar of *Osteospermum* plant as shown and described herein.

* * * * *